(12) United States Patent
McAlister et al.

(10) Patent No.: US 9,437,407 B2
(45) Date of Patent: Sep. 6, 2016

(54) MASS SPECTROMETRY FOR MULTIPLEXED QUANTITATION USING MULTIPLE FREQUENCY NOTCHES

(71) Applicant: President and Fellows of Harvard College, Cambridge, MA (US)

(72) Inventors: Graeme Conrad McAlister, Cambridge, MA (US); Wilhelm Haas, Cambridge, MA (US); Steven P. Gygi, Foxborough, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 468 days.

(21) Appl. No.: 13/901,137

(22) Filed: May 23, 2013

(65) Prior Publication Data

US 2013/0334414 A1    Dec. 19, 2013

Related U.S. Application Data

(60) Provisional application No. 61/650,976, filed on May 23, 2012.

(51) Int. Cl.
*H01J 49/00* (2006.01)
*G01N 33/50* (2006.01)

(52) U.S. Cl.
CPC ........... *H01J 49/0031* (2013.01); *G01N 33/50* (2013.01); *G01N 2560/00* (2013.01)

(58) Field of Classification Search
CPC ............... H01J 49/004; H01J 49/0027; H01J 49/0031; H01J 49/0036
See application file for complete search history.

(56) References Cited

U.S. PATENT DOCUMENTS

| | | | |
|---|---|---|---|
| 4,849,628 A | 7/1989 | Mcluckey et al. | |
| 5,696,376 A | 12/1997 | Doroshenko et al. | |
| 7,569,814 B2 | 8/2009 | Hashimoto et al. | |
| 7,919,745 B2 * | 4/2011 | Shilov et al. | 250/281 |
| 2004/0072251 A1 | 4/2004 | Anderson | |
| 2005/0242278 A1 | 11/2005 | Syage et al. | |
| 2007/0084994 A1 | 4/2007 | Wang et al. | |

(Continued)

FOREIGN PATENT DOCUMENTS

WO    WO 2012/051392 A2    4/2012
WO    WO 2012/164378 A2    12/2012

OTHER PUBLICATIONS

Savitski et al. "Delayed Fragmentation and Optimized Isolation Width Settings for Improvement of Protein Identification and Accuracy of Isobaric Mass Tag Quantification on Orbitrap-Type Mass Spectrometers" Analytical Chemistry Oct. 21, 2011 83 (23), 8959-896.*

(Continued)

*Primary Examiner* — Brooke Purinton
(74) *Attorney, Agent, or Firm* — Wolf, Greenfield & Sacks, P.C.

(57) ABSTRACT

A method of performing a mass spectrometry analysis includes labeling each of a plurality of samples with a corresponding chemical tag; forming a first plurality of ions from molecules in the samples; selecting a subset of the first plurality of ions, the subset being selected by isolating ions of the first plurality of ions in a plurality of ranges of mass-to-charge; forming a second plurality of ions by fragmenting ions in the subset; and measuring information indicative of a quantity of each of the plurality of chemical tags present in each of the plurality of samples.

6 Claims, 9 Drawing Sheets

(56) References Cited

U.S. PATENT DOCUMENTS

| | | |
|---|---|---|
| 2008/0044857 A1 | 2/2008 | Anderson |
| 2008/0230691 A1 | 9/2008 | Hager |
| 2009/0194688 A1 | 8/2009 | Bateman et al. |
| 2009/0283673 A1 | 11/2009 | Shilov et al. |
| 2010/0084547 A1 | 4/2010 | Pringle et al. |
| 2010/0311176 A1 | 12/2010 | Williamson et al. |
| 2011/0111513 A1 | 5/2011 | Baumann et al. |
| 2011/0297823 A1 | 12/2011 | Coon et al. |
| 2012/0091330 A1 | 4/2012 | Coon et al. |
| 2012/0178118 A1 | 7/2012 | Pi et al. |
| 2012/0261568 A1* | 10/2012 | Coon et al. .......... 250/282 |
| 2012/0305762 A1 | 12/2012 | Kaneko et al. |
| 2015/0293058 A1 | 10/2015 | Wuhr et al. |

OTHER PUBLICATIONS

International Search Report and Written Opinion for International Application No. PCT/US2013/040395 mailed Sep. 13, 2013.

International Preliminary Report on Patentability for Application No. PCT/US2013/040395 mailed Dec. 4, 2014.

International Search Report and Written Opinion for Application No. PCT/US2013/066010 mailed Jan. 17, 2014.

International Preliminary Report on Patentability for Application No. PCT/US2013/066010 mailed May 7, 2015.

International Search Report and Written Opinion for Application No. PCT/US2014/023851 mailed Jul. 21, 2014.

International Preliminary Report on Patentability for Application No. PCT/US2014/023851 mailed Sep. 24, 2015.

International Search Report and Written Opinion for Application No. PCT/US2014/041686 mailed Jan. 9, 2015.

Invitation to Pay Additional Fees for Application No. PCT/US2014/041686 mailed Sep. 25, 2014.

\* cited by examiner

MASS SPECTROMETRY FOR MULTIPLEXED QUANTITATION USING MULTIPLE FREQUENCY NOTCHES

RELATED APPLICATIONS

This application claims priority to U.S. Provisional Application No. 61/650,976 filed May 23, 2012 and entitled "Mass Spectrometry for Multiplexed Quantitation Using Multiple Frequency Notches," the entire contents of which are incorporated herein by reference.

GOVERNMENT SUPPORT

This invention was made with government support under 5R01HG003456-07 awarded by National Institutes of Health. The government has certain rights in the invention.

BACKGROUND

Mass spectrometry is a technique that analyzes a sample by identifying the mass-to-charge ratio of constituent parts of the sample. Mass spectrometry (MS) has many applications in the study of proteins, known as proteomics. MS may be used to characterize and identify proteins in a sample or to quantify the amount of particular proteins in a sample.

It is known to analyze proteins, peptides or other large molecules in a multistep process. In the example of a protein analysis, in a first portion of the process, the protein may be broken into smaller pieces, such as peptides. Certain of these peptides may be selected for further processing. Because the peptides are ions (or may be ionized by known processes such as electrospray ionization (ESI), matrix-assisted laser desorption/ionization (MALDI), or any other suitable process), selection may be performed using an ion trap. The ion trap may be controlled with an oscillating excitation signal. Depending on the frequency of oscillation, ions in the trap of different mass-to-charge ratio (m/z—where m is the mass in atomic mass units and z is the number of elemental charges) will be excited with sufficient energy to escape the trap. What remains in the trap following excitation is ions that did not have a mass-to-charge ratio corresponding to the excitation signal. To isolate ions with a particular mass-to-charge ratio, the ion trap may be excited with a signal that sweeps across a range of frequencies except the frequency that excites the ions of interest. Such an excitation signal is said to have a frequency "notch" corresponding to the target ion that is to be isolated.

The selected ions remaining in the trap may be again broken into smaller pieces, generating smaller ions. These ions may then be further processed. Processing may entail selecting and further breaking up the ions. The number of stages at which ions are selected and then broken down again may define the order of the mass spectrometry analysis, such as $MS^2$ or $MS^3$. Regardless of the order, at the end stage, the mass-to-charge distribution of the ions may be measured, providing data from which properties of the compound under analysis may be inferred. The ions prior to a fragmentation are sometimes called "precursor" ions and the ions resulting from a fragmentation are sometimes called "product ions." The mass-to-charge distribution may be acquired for any group of product ions. Moreover, all or a subset of product ions from one stage of MS may be used as precursor for a subsequent stage of MS.

This multistep process may be time consuming. It is known to increase the throughput of a mass spectrometry facility by analyzing multiple samples at the same time, which is sometimes referred to as "multiplexing" the samples. The development of specially designed chemical tags, such as tandem mass tags (TMTs) and isobaric tags for relative and absolute quantitation (iTRAQ), has provided the ability to perform multiplexed quantitation of a plurality of samples simultaneously. Performing a multiplexed quantitation allows the relative quantities of particular proteins or peptides between samples to be determined. For example, multiplexed quantitation may be used to identify differences between two tissue samples, which may comprise thousands of unique proteins.

The chemical tags are included in reagents used to treat peptides as part of sample processing. A different tag may be used for each sample. Each of the plurality of tags is isobaric, meaning they have nominally the same mass. This is achieved by using different isotopes of atoms in the creation of the tags. For example, a first tag may use a Carbon-12 atom at a particular location of the molecule, whereas as second tag may use a Carbon-13 atom—resulting in a weight difference of one atomic mass unit at that particular location. This purposeful selection of particular isotopes may be done at a plurality of locations for a plurality of elements. As a whole, each isotope of each tag is selected so that the different types of tags have the same total mass resulting in tagged precursor ions with nominally the same mass despite being labeled with a different type of tag. The different isotopes are strategically distributed within the tag molecule such that the portion of the tag molecule that will become a reporter ion for each type of tag has a different weight. Thus, when the different types of tags are fragmented during the MS analysis techniques, each type of tag will yield reporter ions with distinguishable mass-to-charge (m/z) ratios. The intensity of the reporter ion signal for a given tag is indicative of the amount of the tagged protein or peptide within the sample. Accordingly, multiple samples may be tagged with different tags and simultaneously analyzed to directly compare the difference in the quantity of particular proteins or peptides in each sample.

In the analysis described above, the multi-step processes serves to reduce reporter ion ratio distortion resulting from the fragmentation of co-isolated interfering ions. In particular, if interfering ions tagged with the same type of tag were not completely ejected from the ion trap during the isolation of the target peptides, reporter ions from the tags of the interfering ions may have contributed to the observed signal. In this case, determining the quantity of the tagged target peptide was difficult due to the reporter ions of the target peptides being indistinguishable from the reporter ions of interfering ions. Accordingly, any interfering ion that was co-isolated with the target peptide destroyed the ability to accurately determine the quantity of the target peptide in the sample.

FIG. 1 illustrates this interference problem. In FIG. 1A, a complex mixture of LysC TMT-labeled yeast peptides (ratios 10:4:1:1:4:10) was mixed with a complex mixture of LysC TMT-labeled human peptides (ratios 1:1:1:0:0:0) and analyzed in a series of LC-MS2 and LC-MS2/MS3 based analyses. In FIG. 1B TMT-labeled peptide (NAAWLV-FANK—ratios 10:4:1:1:4:10) was interrogated in back-to-back scans using: (1) MS2 scans that fragmented the MS1 precursors using either CID-NCE35 or HCD-NCE45. (2) An MS3 scan that fragmented the MS1 precursor with CID-NCE35, isolated a single MS2 product ion, and then fragmented that ion population using HCD-NCE60. And, (3) an MS3 scan that isolated multiple MS2 product ions, and then fragmented that population using HCD-NCE50.

FIG. 1A shows a complex mixture of LysC TMT-labeled yeast peptides mixes in a one-to-one ratio with a complex mixture of LysC TMT-labeled human peptides. The yeast peptides, for the purposes of this illustrative example, are considered the target and the human peptides generate the interfering ions. The peptide NAAWLVFANK (wherein each letter of the sequence represents an amino acid) of the yeast sample is labeled with one of six TMT tags. The six tags are used in a 10:4:1:1:4:10 ratio and mixed together to make the complex mixture. The human sample is labeled with the six different TMT tags with a 1:1:1:0:0:0 ratio. If there was no interference from the human peptides, the resulting MS spectrum of the tags would perfectly match the original ratio of the target sample, i.e. 10:4:1:1:4:10. This ideal spectrum is illustrated by the MS spectrum on the bottom right of FIG. 1A. However, with interference from the human sample, the MS spectrum is not accurate, as illustrated by the MS spectrum in the top right of FIG. 1A. Due to contributions from the first three tags used to label the peptides of the human sample, the intensity of the peaks associated with the m/z value of the first three tags are not accurate. This interference destroys the ability to accurately determine the relative ratios of each tag used in the yeast sample.

This interference problem is also illustrated in the top spectra of FIG. 1B based on experimental data. The spectrum on the left represents the $MS^2$ product ion spectrum of the above described sample wherein the $MS^2$ precursor ion is fragmented using collision induced dissociation (CID) with a normalized collision energy (NCE) of 35% (CID-NCE35) or high energy beam type dissociation (HCD) with an NCE of 45% (HCD-NCE45). The spectrum on the top right of FIG. 1B represents a portion of the $MS^2$ product ion spectrum showing only the m/z value range from 125-133, which is the range encompassing the m/z values of the six different reporter ions of the six different types of TMT tags used. As discussed above, the ratio of the intensity of the first tag to the third tag should be 10:1 in the absence of interference from the human peptides. In this particular experiment, the ratio is 4.6:1, which is inaccurate by more than a factor of two. This dramatic inaccuracy of the relative quantitation measurement illustrates the need to find a solution to this interference problem caused by co-isolated precursors.

BRIEF DESCRIPTION OF THE DRAWINGS

Aspects of the invention are described with reference to illustrative embodiments and the following drawings in which like reference characters represent like elements, and wherein.

DETAILED DESCRIPTION

The problem of co-isolated peptides may be remedied by employing an additional layer of gas-phase selectivity, i.e., using an $MS^3$ technique rather than an $MS^2$ technique. The target $MS^2$ precursor ions, along with the interfering ions, may be fragmented into a relatively homogeneous mixture of $MS^2$ product ions with a wide range of m/z values. The fragmentation process (e.g., CID, HCD, proton transfer reaction (PTR), etc.) may be purposefully selected to reduce or minimize the likelihood that the interfering ions will undergo the same transformation as the $MS^2$ precursor ions. As such, following the transformation, the likelihood of co-isolating $MS^2$ product ions that belong to both the target ion and any interfering ion is low. One or more of the resulting $MS^2$ product ions may be selected, without including any interfering ions, as the $MS^3$ precursor ion to an additional fragmentation and $MS^3$ analysis.

Figure 1A:
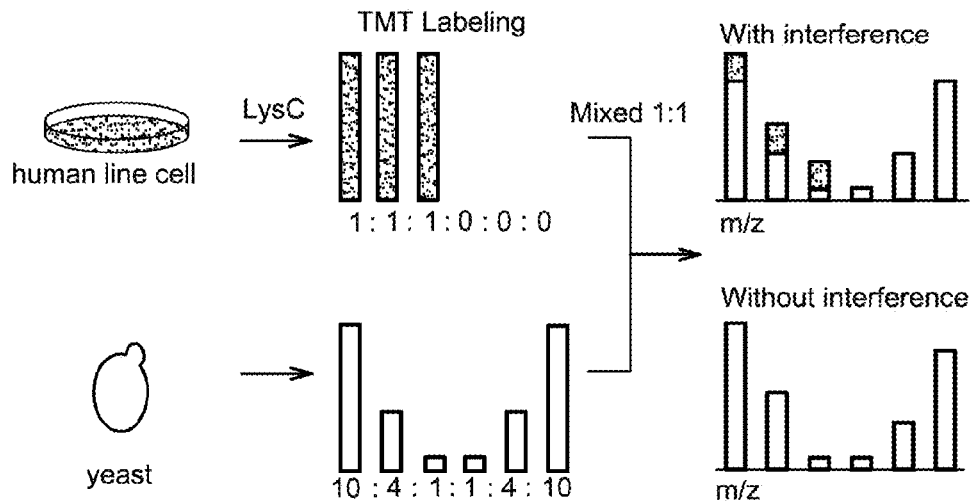
FIG. 1A shows a complex mixture of LysC TMT-labeled yeast peptides mixes in a one-to-one ratio with a complex mixture of LysC TMT-labeled human peptides.
Figure 1B:
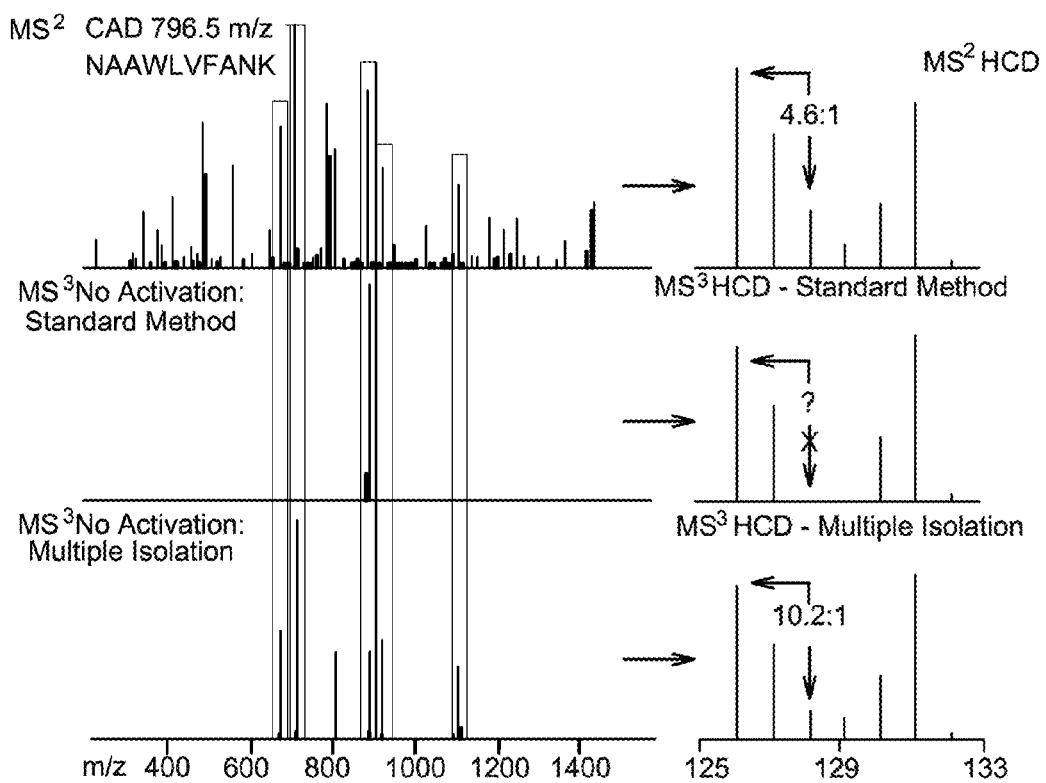
FIG. 1B shows TMT-labeled peptide (NAAWLVFANK—ratios 10:4:1:1:4:10) interrogated in back-to-back scans using: (1) MS2 scans that fragmented the MS1 precursors using either CID-NCE35 or HCD-NCE45; (2) an MS3 scan that fragmented the MS1 precursor with CID-NCE35, isolated a single MS2 product ion, and then fragmented that ion population using HCD-NCE60; and, (3) an MS3 scan that isolated multiple MS2 product ions, and then fragmented that population using HCD-NCE50.

The middle spectra of FIG. 1B illustrates a problem that arises if only a single $MS^2$ product ion is selected as the $MS^3$ precursor ions for the $MS^3$ technique. The target population and the interfering ions were simultaneously fragmented using CID, resulting in a spectrum similar to the top spectrum in FIG. 1B. The middle $MS^2$ spectrum on the left illustrates the most intense fragment ion being isolated from the rest of the $MS^2$ fragment ion population. Isolation of a single m/z range is achieved using an isolation waveform for the ion trap of the MS apparatus and will be discussed in detail below. Following isolation of the primary product ion, that population of product ions is fragmented and the resulting purified reporter ion population is analyzed.

Moreover, the inventors have recognized and appreciated that, though isolation techniques counter the reporter ion distortion caused by interfering ions, those gains come at the cost of decreased sensitivity. Precursor-to-reporter ion conversion efficiency drops substantially with the inclusion of each additional round of gas-phase manipulation and selectivity. When selecting a single product ion from amongst the wide range of product ions that are typically produced during these transformative processes, it can be very difficult to capture even a moderate amount of the product signal in the precursor population of the next round of $MS^n$ analysis. This decrease in precursor ions for the subsequent fragmentation results in a very small number of reporter ions being produced by the various tags. Thus, in the case of $MS^3$, the ability to accurately determine the relative quantities of each tag's reporter ion using the $MS^3$ spectrum is seriously hindered (see the middle right spectrum of FIG. 1B). In the sample $MS^3$ spectrum shown, no reporter ions for the third or fourth tag were detected due to the low yield of precursor ions resulting in a quantity of reporter ions below the detection limits of the spectrometer used. In this scenario, it impossible to determine the ratio of the intensity of the signal associated with the first and third tags.

The inventors have further recognized and appreciated that high throughput may be achieved in spectrometry, while retaining accuracy, by selecting multiple m/z ranges (also called "notches") to co-isolate multiple $MS^2$ product ions to be used as $MS^3$ precursors. Selecting multiple notches may increase the number of $MS^3$ precursor ions. By co-isolating multiple $MS^3$ precursor ions, the bottleneck associated with additional rounds of gas-phase selectivity is avoided—that is, the precursor-to-reporter ion conversion efficiency is significantly increased by conveying more ions through this additional round of gas-phase selectivity. This translates into improved reporter ion dynamic range, reduced reporter variance, and ultimately more high-quality protein-level quantitative measurements. This technique is not limited to $MS^3$ applications and may be used for $MS^n$ techniques with any number (n) of stages.

By way of example, the bottom spectra of FIG. 1B illustrates six different m/z ranges, each corresponding to some of the most intense $MS^2$ fragment ions. By using all the ions from these six notches as $MS^3$ precursor ions, the intensity of the signals corresponding to the reporter ions of each of the TMT tags is significantly increased. Accordingly, the interference from the human peptides may be avoided by adding the extra fragmentation step without decreasing the sensitivity of the final measurement. The $MS^3$ spectrum on the bottom right of FIG. 1B illustrates the high quality, interference free signal that results from this technique. The ratio between the first and third tags is accurately determined to be 10.2:1, which is very close to the actual 10:1 ratio.

Figure 2A:
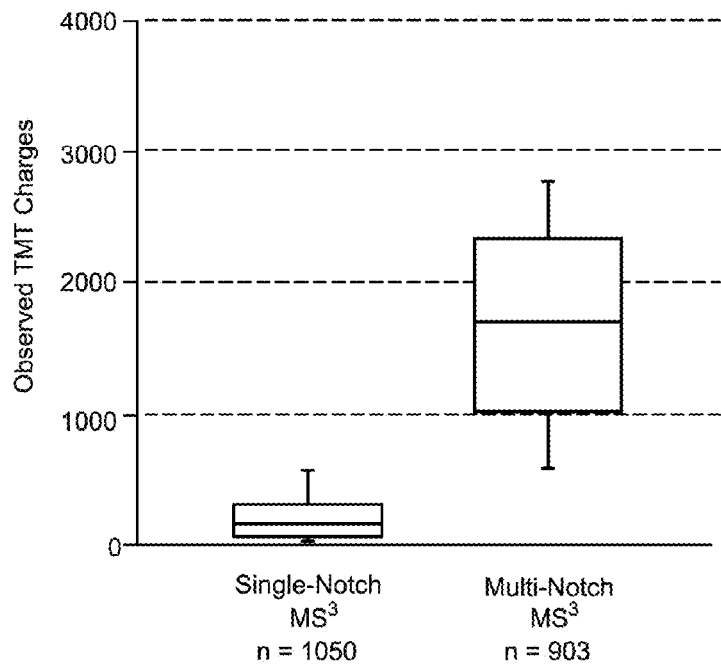
FIG. 2A illustrates the significant increase in signal that results from using a multi-notch $MS^3$ approach as opposed to a single notch $MS^3$ approach.
Figure 2B:
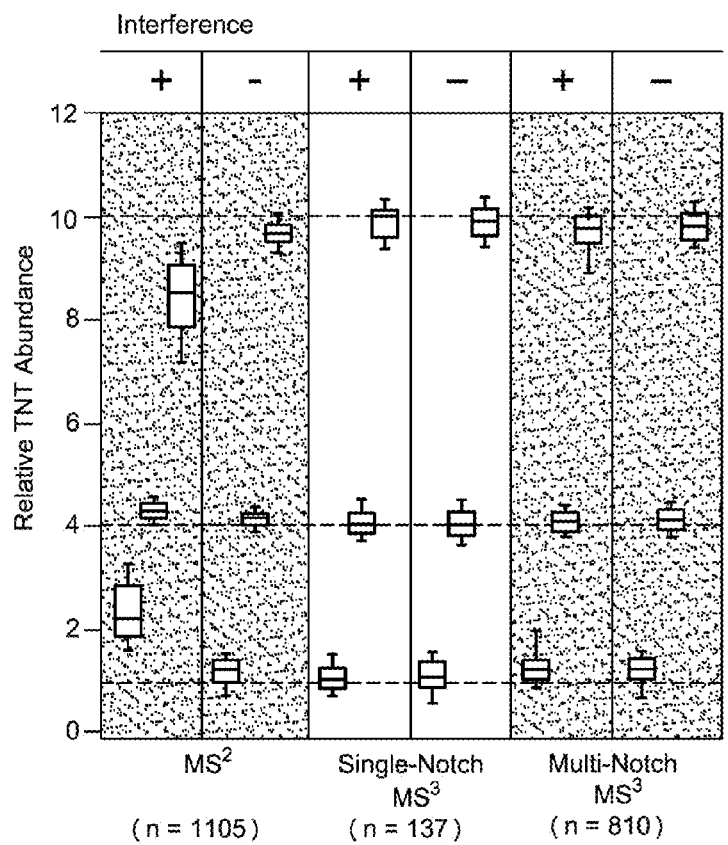
FIG. 2B illustrates the distribution of TMT abundances as a function of instrument method and the occurrence of interference.

In FIG. 2, the TMT-labeled yeast/human complex mixture was analyzed by LC-MS2 and LC-MS2/MS3 in consecutive analyses. Separate LC-MS2/MS3 analyses were performed using the single-notch MS3 method and the multi-notch method for co-isolating and fragmenting multiple MS2 fragment ions. In FIG. 2A, illustrates the distribution of TMT signals the single-notch and multi-notch MS3 analyses. In FIG. 2B, illustrates the distribution of TMT abundances as a function of instrument method and the occurrence of interference.

FIG. 2A illustrates the significant increase in signal that results from using a multi-notch $MS^3$ approach as opposed to a single notch $MS^3$ approach. The inventors have experimentally realized up to an eight-fold increase in the number of observed reporter ions, though the increase may be greater depending on the number of notches and the type of peptides being investigated.

FIG. 2B illustrates the distribution of TMT abundances as a function of instrument method and the occurrence of interference.

Figure 3A:
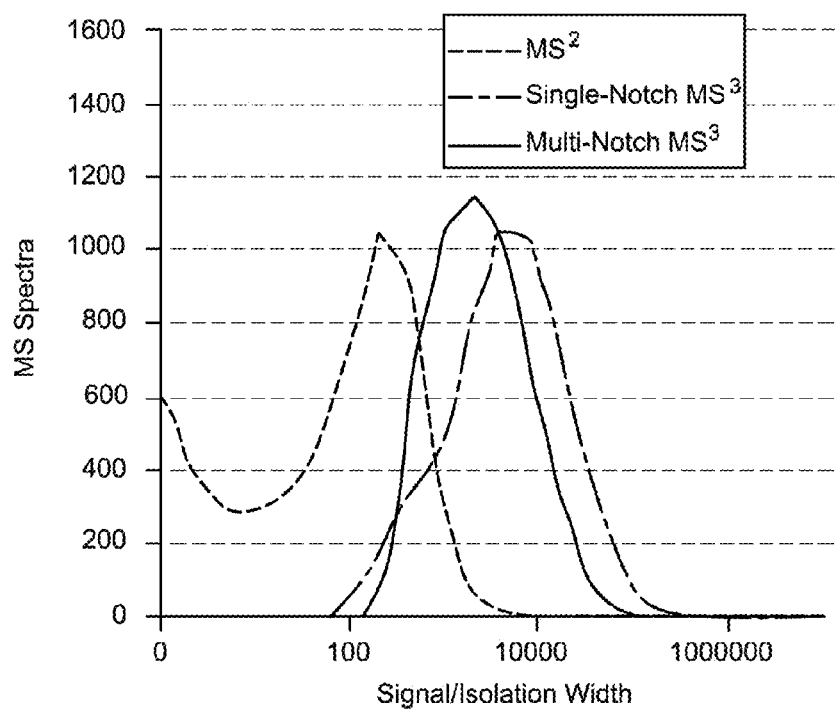
FIG. 3A illustrates the distribution between $MS^3$ precursor signal and net isolation width for the single-notch method and "multi-notch" method, as-well-as the distribution between $MS^2$ product ion signal and $MS^2$ mass range for the standard Liquid Chromatography-$MS^2$ ($LC-MS^2$) method.
Figure 3B:
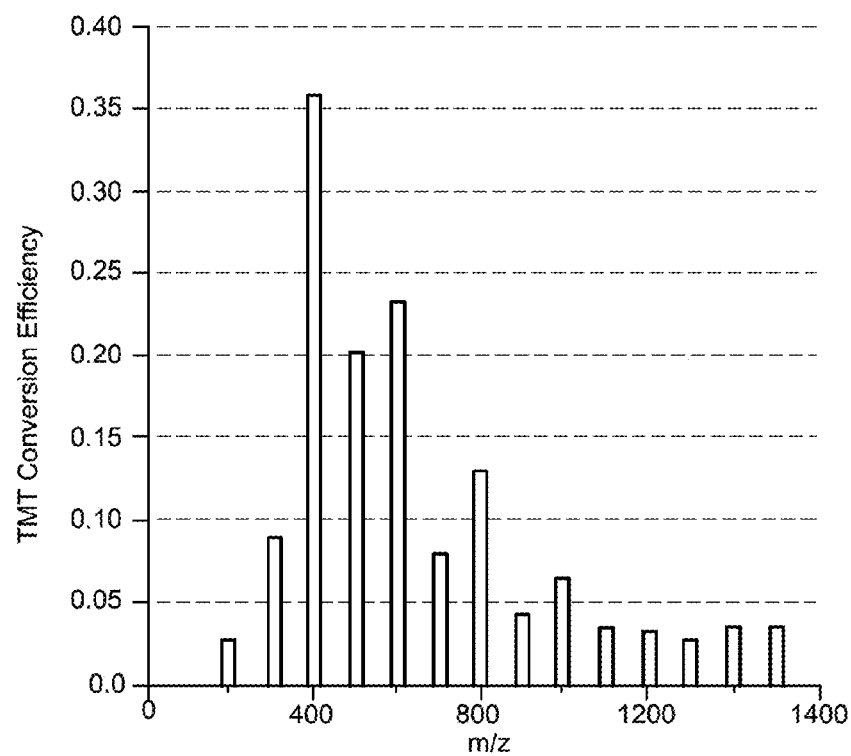
FIG. 3B illustrates the conversion efficiency between TMT-labeled $MS^2$ fragments and TMT reporter ions (produced via HCD) plotted as a function of $MS^2$ fragment m/z value.
Figure 3C:
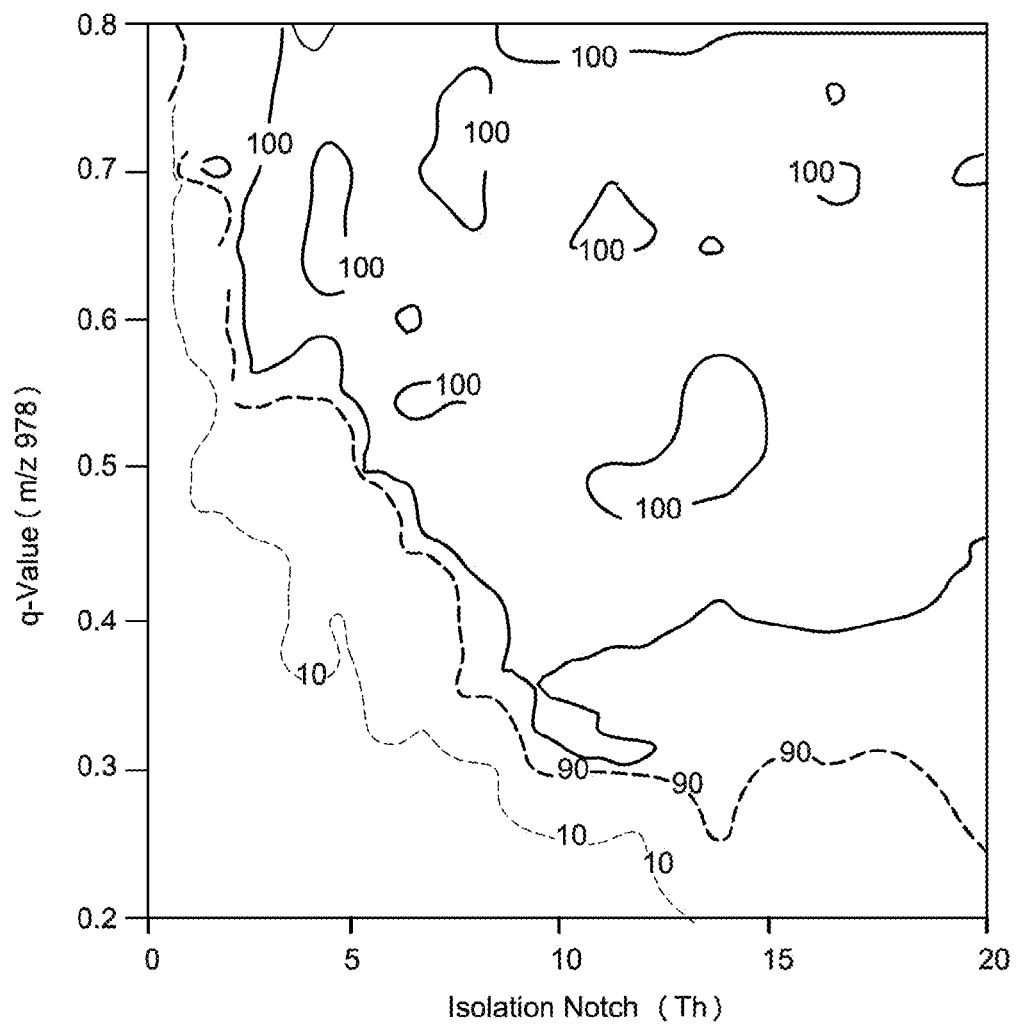
FIG. 3C illustrates the isolation efficiency plotted as a function of precursor q-value and isolation notch width.

FIG. 3A illustrates the distribution between $MS^3$ precursor signal and net isolation width for the single-notch method and "multi-notch" method, as-well-as the distribution between $MS^2$ product ion signal and $MS^2$ mass range for the standard Liquid Chromatography-$MS^2$ (LC-$MS^2$) method. FIG. 3B illustrates the conversion efficiency between TMT-labeled $MS^2$ fragments and TMT reporter ions (produced via HCD) was plotted as a function of $MS^2$ fragment m/z value. FIG. 3C illustrates the isolation efficiency was plotted as a function of precursor q-value and isolation notch width.

Figures 4A, 4B, 4C:
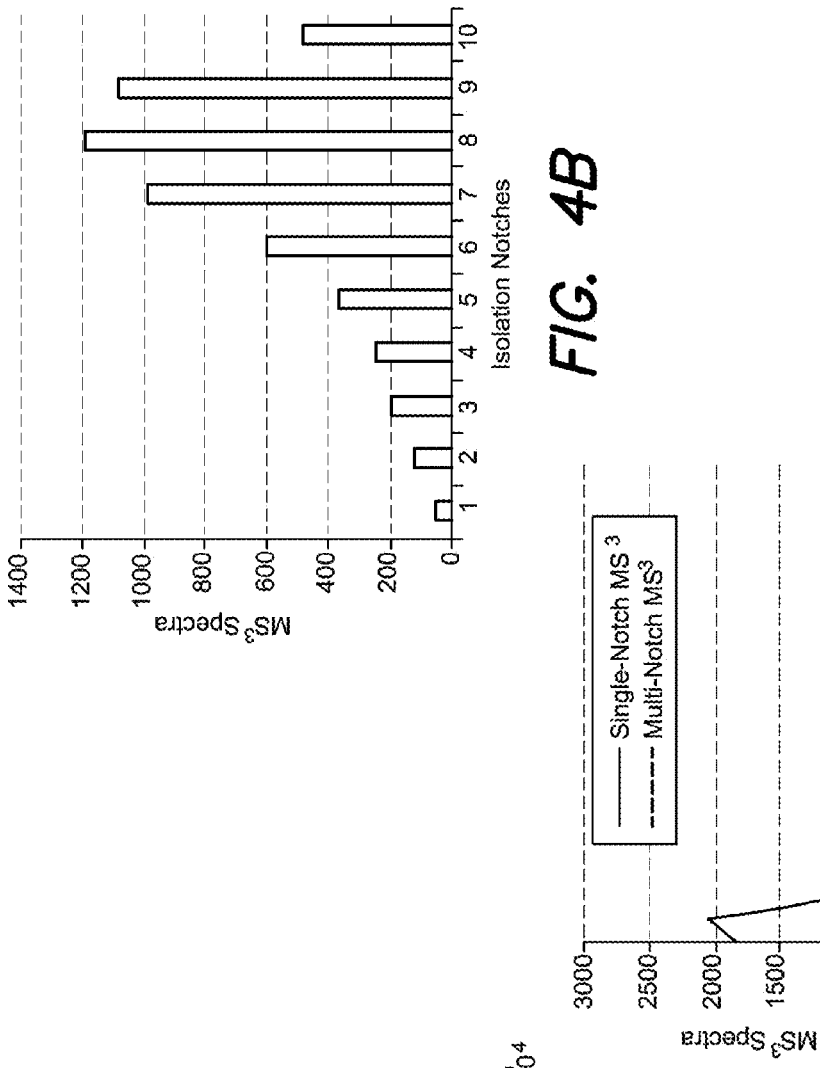
FIG. 4A illustrates a scatter plot comparing the predicted total MS3 TMT signal for the "multi-notch" method against the actual TMT signal.
FIG. 4B illustrates a histogram of the number of isolation notches in the "multi-notch" MS3 isolation waveforms.
FIG. 4C illustrates the distribution of the fraction of the MS2 product ion population included in the MS3 precursor population for the single-notch and "multi-notch" MS.

In FIG. 4, the TMT-labeled yeast/human complex mixture was analyzed separately using the single-notch LC-MS2/MS3 method and our "multi-notch" method. FIG. 4A illustrates a scatter plot comparing the predicted total MS3 TMT signal for the "multi-notch" method against the actual TMT signal. FIG. 4B illustrates a histogram of the number of isolation notches in the "multi-notch" MS3 isolation waveforms. FIG. 4C illustrates the distribution of the fraction of the MS2 product ion population included in the MS3 precursor population for the single-notch and "multi-notch" MS.

Figure 5:
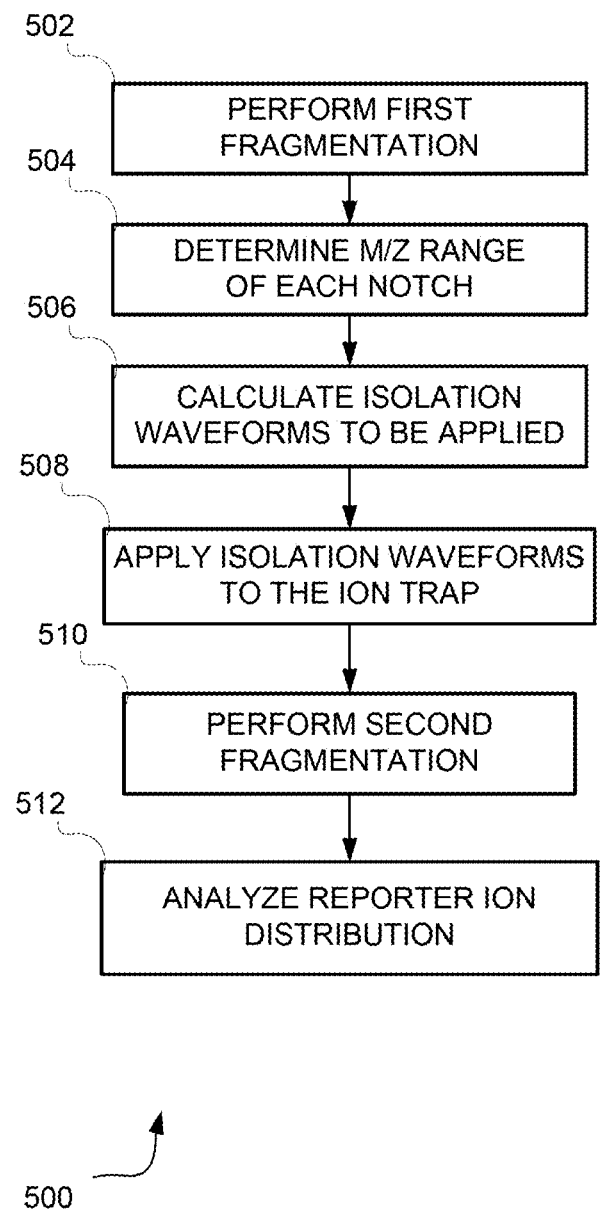
FIG. 5 illustrates a method 500 of one embodiment of the present application.

FIG. 4A provides an example scatter plot comparing the predicted total $MS^3$ TMT signal for the "multi-notch" method against the actual TMT signal. FIG. 4B provides an example histogram showing the number $MS^2$ product ions that become $MS^3$ precursor ions as a function of the number of isolation notches in the "multi-notch" $MS^3$ isolation waveforms. FIG. 4C provides an example illustrating the difference between the distribution of the fraction of $MS^2$ product ions that are included in the $MS^3$ precursor population in a single-notch $MS^3$ approach versus a multi-notch $MS^3$ approach. The precursor-to-reporter ion conversion efficiency is significantly increased by conveying more ions using multiple m/z ranges. FIG. 5 illustrates a method 500 of one embodiment of the present application. Method 500 may be implemented using any suitable apparatus for isolating ions for further processing. For example, the apparatus could be a quadrapole ion trap, a Fourier transform ion cyclotron resonance (FTICR) MS, an orbitrap MS or other ion trap.

At act 502, a first fragmentation is performed. This may be done in any suitable way. By way of example and not limitation, the $MS^2$ precursor ions may be fragmented by collision induced dissociation (CID), proton transfer reaction (PTR), infrared multi-photon dissociation (IRMPD), ultraviolet photon dissociation (UVPD), electron transfer dissociation (ETD), electron capture dissociation (ECD), high energy beam type dissociation (HCD), surface induced dissociation (SID), or pulsed-q dissociation (PQD). Embodiments are not limited to any particular process of fragmentation.

At act 504, the m/z range may be determined for each notch. For example, a minimum and maximum m/z value may be calculated. As another example, a center m/z value and a corresponding width may be determined. The calculation of the m/z range for each notch may be done in any suitable way. An exemplary embodiment of this calculation is described in connection with FIG. 6.

At act 506, the isolation waveforms for the ion trap are calculated based on the m/z ranges determined in act 504.

The isolation waveforms may be calculated in any suitable way. For example, characteristic frequencies, q, for each relevant mass range may be determined based on an empirically determined relationship between a particular m/z value and q (see, for example, FIG. 3C).

At act 508, the isolation waveforms determined in act 506 are applied to the ion trap. This may be done in any suitable way. For example, a radio frequency (RF) signal generator may be used to generate the calculated isolation waveforms. The isolation waveforms may be applied simultaneously, or may be applied in a time series, one after the other.

At act 510, a second fragmentation is performed. The second fragmentation fragments the $MS^2$ product ions that were isolated by the isolation waveforms. This second fragmentation may be done in any suitable way. By way of example and not limitation, the $MS^3$ precursor ions may be fragmented by collision induced dissociation (CID), proton transfer reaction (PTR), infrared multi-photon dissociation (IRMPD), ultraviolet photon dissociation (UVPD), electron transfer dissociation (ETD), electron capture dissociation (ECD), high energy beam type dissociation (HCD), surface induced dissociation (SID), or pulsed-q dissociation (PQD). Embodiments are not limited to any particular process of fragmentation.

At act 512, the results of the second fragmentation are analyzed. In particular, the distribution and relative intensities of the reporter ion signals associated with the different types of tags may be analyzed. The other $MS^3$ product ions not associated with the chemical tags may also be analyzed to determine other characteristics of the isolated peptides. Embodiments of the invention are not limited to any particular type of analysis.

Figure 6:
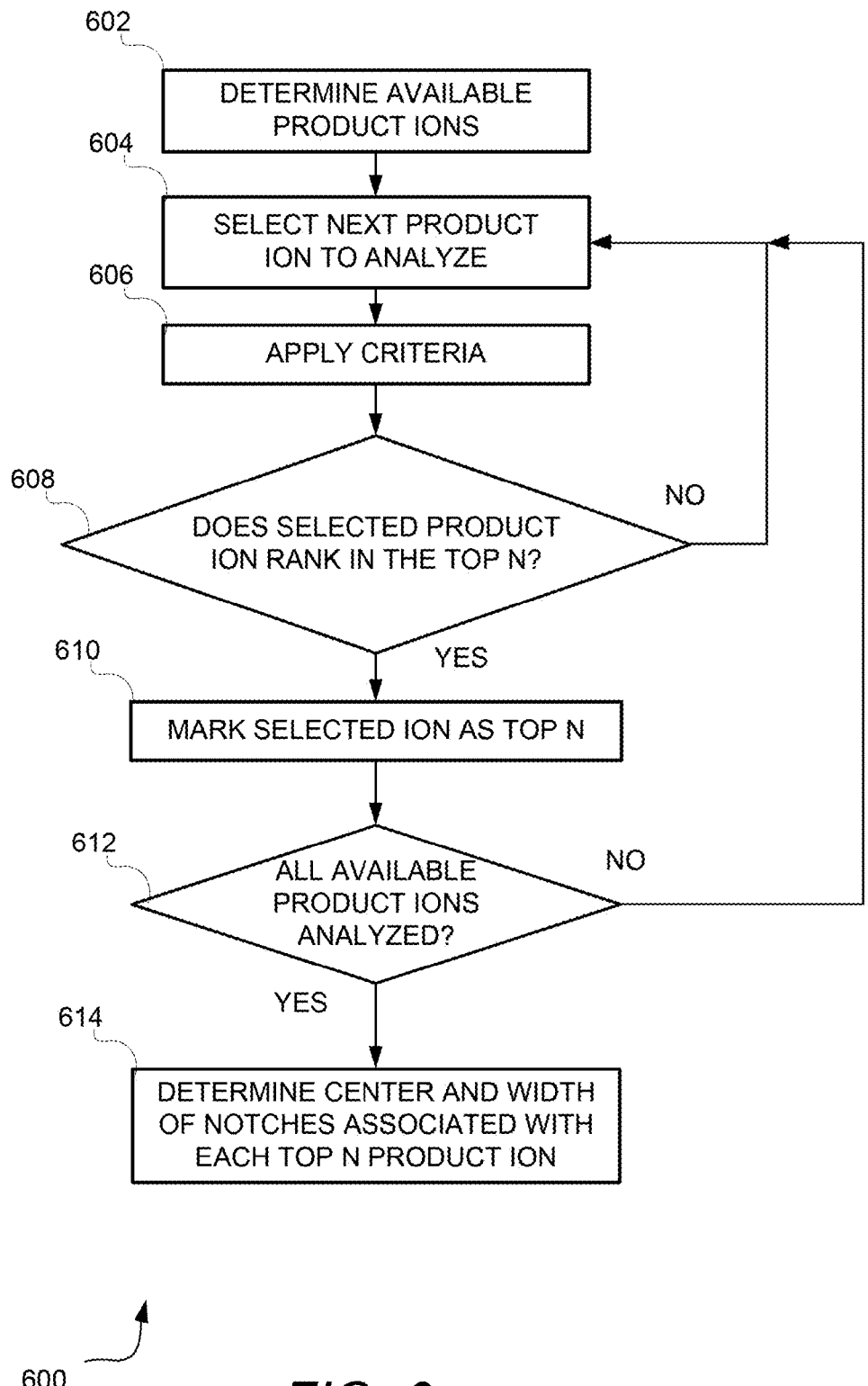
FIG. 6 illustrates an exemplary embodiment for determining the center and width of each notch for isolating product ions.

FIG. 6 illustrates an exemplary embodiment for determining the center and width of each notch for isolating product ions. At act 602, the product ions that are available are determined. This may be done in any suitable way. For example, an experimental analysis of the product ion spectrum may be performed. This product ion spectrum may be used to identify potential product ions to be isolated for use as precursor ions in the next stage of the MS procedure. Certain filters may be applied at this stage. For example, only product ions with an intensity above a threshold may be considered for use as a precursor ion. Also, a filter based on m/z value may be used. For example, product ions with m/z value less than a threshold may not be considered as precursor ions. This threshold may be, by way of example and not limitation, 400 Daltons.

In some embodiments the available product ions for isolation may be determined without performing an analysis of the product ions. For example, if a particular diagnostic test that produces known product ions is being performed, the available product ions may be stored in the analysis software before the analysis begins.

At act 604, the next product ion of the available ions is selected. In the case of the first product ion of the plurality of available ions being considered prior to any other of the plurality of available product ions, this is not the "next" product ion but the "first" product ion. This is the beginning of a loop that will iterate through all the determined available product ions being considered as candidates for precursor ions of the next MS stage.

At act 606, one or more criterion are applied to the selected product ion. Any suitable criteria may be used to analyze the selected product ions suitability for use as a precursor ion. For example, properties of the selected product ion may be considered, such as its m/z value, the intensity within the product ion spectrum, the charge, and the mass. Other criteria may also be considered, such as the signal to noise ratio of the selected product ion versus the nearby noise from other ions.

Some embodiments estimate the conversion efficiency between the selected product ion and the $MS^3$ reporter ion population. For example, FIG. 3B illustrates the conversion efficiency as the probability that a product ion of a given m/z value will generate a reporter ion associated with the chemical tag.

In some embodiments, these estimations may take into account the chromatographic retention time of the selected product ion, the species of the selected product ion (e.g., peptide, lipid, carbohydrate, etc.), and the structure of the isobaric label.

Some embodiments take into account the distance to other product ions. For example, it may be disadvantageous to choose precursor ions that are far apart because doing so may result in increased window size for each notch. This increase in window size may result in an increase in co-isolation of interfering ions that would preferably not be isolated along with the precursor ions.

After applying at least one criterion to the selected product ion, it is determined at act 608 whether the selected product ion ranks in the top N, where N is the number of notches that may be used to isolate precursor ions. If the selected product ion does not rank in the top N ions, then the method loops back to act 604 and the next available product ion is selected. If the selected product ion ranks in the top N ions, then the method continues at act 610 where the selected ion is marked as a top N ion. Marking the product ion may be done in any suitable way. For example, a list of the top N product ions may be maintained. Alternatively, a complete ranking of every available product ion may be maintained.

At act 612, it is determined whether all available product ions have been analyzed. If not, the method loops back to act 604 where the next available product ion is selected. If all available product ions have been analyzed, then the method continues to act 614 to determine the center and width of the N notches associated with the top N available product ions. This may be done in any suitable way. For example, any of the aforementioned product ion characteristics or product ion characteristics may be used in determining the center and width of the notches. The characteristics of the ion trap and the generators of the isolation waveforms may also be taken into account. For example, there may be limitations on the width of the notch based on the characteristics of the RF signal generator.

By culling the potential $MS^3$ precursor population to only high performing $MS^2$ product ions, as described in FIG. 6, embodiments of the invention maintain the specificity of the single-notch $MS^3$ implementation (see, e.g., FIG. 3A) while increasing the intensity of the reporter ions associated with the chemical tags. The number of $MS^2$ product ions included in each $MS^3$ precursor population varies from scan-to-scan depending upon various $MS^2$ spectral characteristics (e.g., $MS^2$ product ion distribution—FIG. 4B). In another embodiments, various mass ranges that are likely to contain a high density of interfering ions are excluded (e.g., the low mass range and the range in the immediate vicinity of the $MS^1$ precursor). In other embodiments, instead using these algorithms to determine which $MS^2$ product ions to include in the $MS^3$ precursor population on-line, we may input an inclusion list of $MS^2$ ions to consider prior to the actual analysis.

Figure 7:
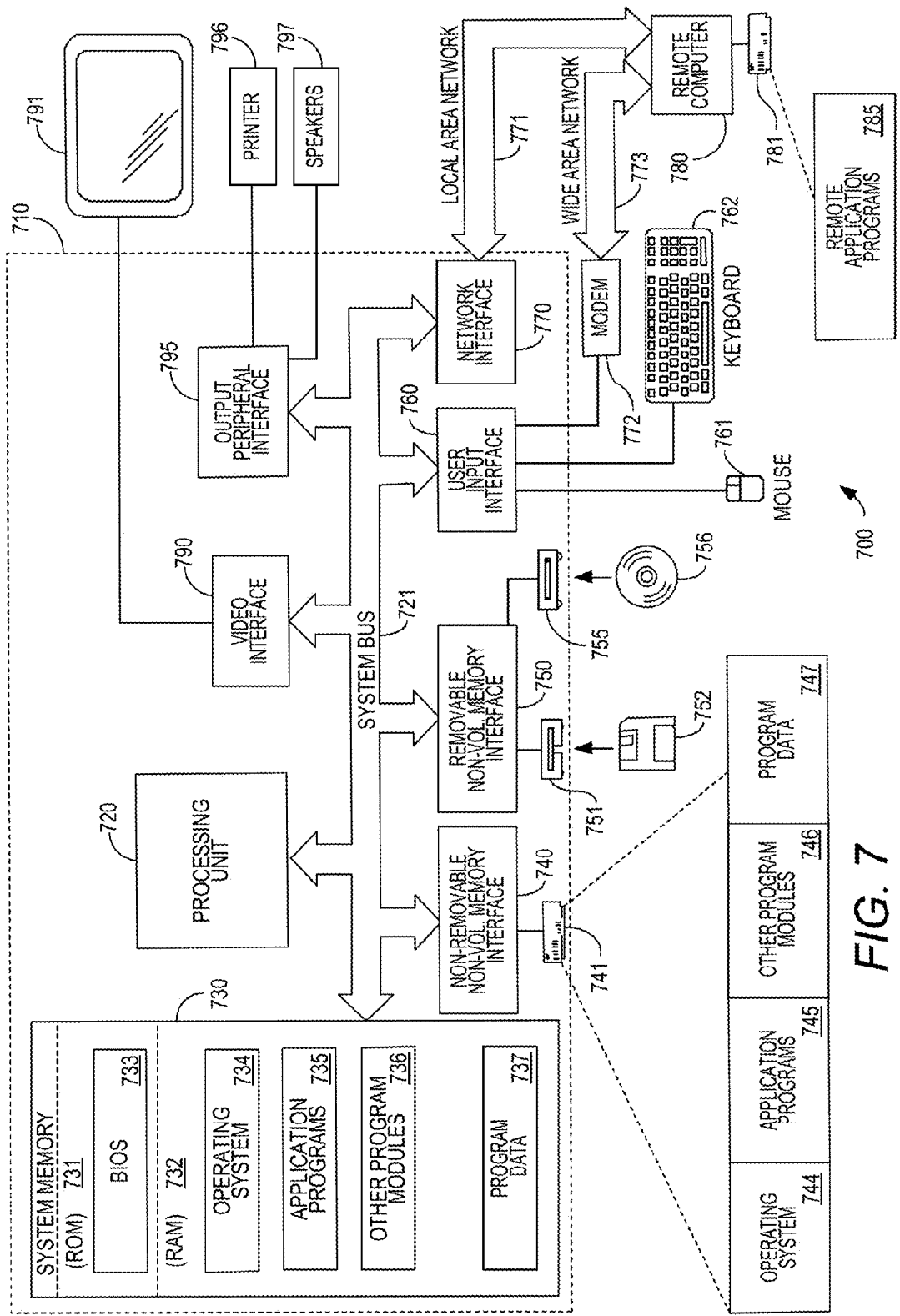
FIG. 7 illustrates an example of a suitable computing system environment 700 on which embodiments of the invention may be implemented.

FIG. 7 illustrates an example of a suitable computing system environment 700 on which embodiments of the invention may be implemented. Embodiments of the invention, such as the methods described in FIG. 5 and FIG. 6, may be implemented partially or entirely in computing system environment 700. For example, such a computing system environment may execute software controlled a mass spectrometer used in performing some or all of the acts in FIG. 5. Such a computing system environment alternatively or additionally may execute a tool performing some or all of the acts in FIG. 6 to determine appropriate notches. Parameters associated with these determined notches may then be programmed into a mass spectrometer.

The computing system environment 700 is only one example of a suitable computing environment and is not intended to suggest any limitation as to the scope of use or functionality of the invention. Neither should the computing environment 700 be interpreted as having any dependency or requirement relating to any one or combination of components illustrated in the exemplary operating environment 700.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 7, an exemplary system for implementing embodiments of the invention includes a general purpose computing device in the form of a computer 710. Components of computer 710 may include, but are not limited to, a processing unit 720, a system memory 730, and a system bus 721 that couples various system components including the system memory to the processing unit 720. The system bus 721 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 710 typically includes a variety of computer readable media. Computer readable media can be any available media that can be accessed by computer 710 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 710. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 730 includes computer storage media in the form of volatile and/or nonvolatile memory such as read only memory (ROM) 731 and random access memory (RAM) 732. A basic input/output system 733 (BIOS), containing the basic routines that help to transfer information between elements within computer 710, such as during start-up, is typically stored in ROM 731. RAM 732 typically contains data and/or program modules that are immediately accessible to and/or presently being operated on by processing unit 720. By way of example, and not limitation, FIG. 7 illustrates operating system 734, application programs 735, other program modules 736, and program data 737.

The computer 710 may also include other removable/non-removable, volatile/nonvolatile computer storage media. By way of example only, FIG. 7 illustrates a hard disk drive 741 that reads from or writes to non-removable, nonvolatile magnetic media, a magnetic disk drive 751 that reads from or writes to a removable, nonvolatile magnetic disk 752, and an optical disk drive 755 that reads from or writes to a removable, nonvolatile optical disk 756 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 741 is typically connected to the system bus 721 through an non-removable memory interface such as interface 740, and magnetic disk drive 751 and optical disk drive 755 are typically connected to the system bus 721 by a removable memory interface, such as interface 750.

The drives and their associated computer storage media discussed above and illustrated in FIG. 7, provide storage of computer readable instructions, data structures, program modules and other data for the computer 710. In FIG. 7, for example, hard disk drive 741 is illustrated as storing operating system 744, application programs 745, other program modules 746, and program data 747. Note that these components can either be the same as or different from operating system 734, application programs 735, other program modules 736, and program data 737. Operating system 744, application programs 745, other program modules 746, and program data 747 are given different numbers here to illustrate that, at a minimum, they are different copies. A user may enter commands and information into the computer 710 through input devices such as a keyboard 762 and pointing device 761, commonly referred to as a mouse, trackball or touch pad. Other input devices (not shown) may include a microphone, joystick, game pad, satellite dish, scanner, or the like. These and other input devices are often connected to the processing unit 720 through a user input interface 760 that is coupled to the system bus, but may be connected by other interface and bus structures, such as a parallel port, game port or a universal serial bus (USB). A monitor 791 or other type of display device is also connected to the system bus 721 via an interface, such as a video interface 790. In addition to the monitor, computers may also include other peripheral output devices such as speakers 797 and printer 796, which may be connected through a output peripheral interface 795.

The computer 710 may operate in a networked environment using logical connections to one or more remote computers, such as a remote computer 780. The remote computer 780 may be a personal computer, a server, a router, a network PC, a peer device or other common network node, and typically includes many or all of the elements described above relative to the computer 710, although only a memory storage device 781 has been illustrated in FIG. 7. The logical connections depicted in FIG. 7 include a local area network (LAN) 771 and a wide area network (WAN) 773, but may also include other networks. Such networking environments are commonplace in offices, enterprise-wide computer networks, intranets and the Internet.

When used in a LAN networking environment, the computer 710 is connected to the LAN 771 through a network interface or adapter 770. When used in a WAN networking environment, the computer 710 typically includes a modem 772 or other means for establishing communications over the WAN 773, such as the Internet. The modem 772, which may be internal or external, may be connected to the system bus 721 via the user input interface 760, or other appropriate mechanism. In a networked environment, program modules depicted relative to the computer 710, or portions thereof, may be stored in the remote memory storage device. By way of example, and not limitation, FIG. 7 illustrates remote application programs 785 as residing on memory device 781. It will be appreciated that the network connections shown are exemplary and other means of establishing a communications link between the computers may be used.

Figure 8:
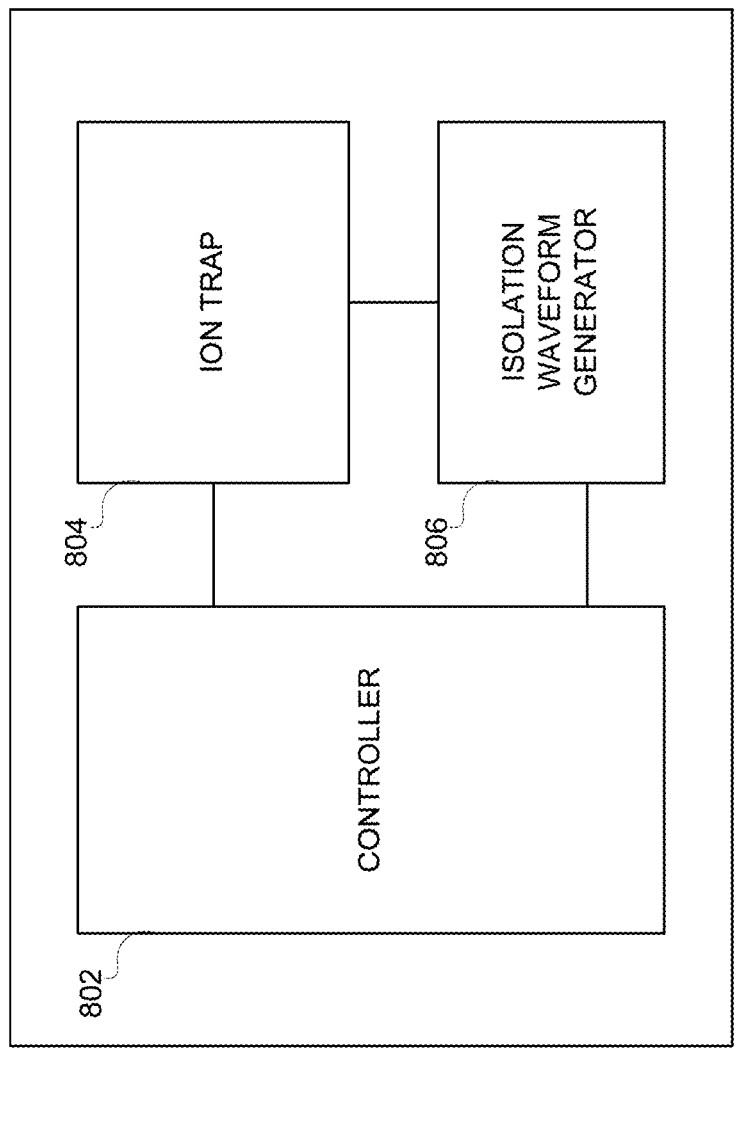
FIG. 8 illustrates a block diagram of a mass spectroscopy apparatus 800 that may perform aspects of embodiments of the present invention.

FIG. 8 illustrates a block diagram of a mass spectroscopy apparatus 800 that may perform aspects of embodiments of the present invention. The apparatus 800 itself may also embody aspects of the present invention. Apparatus 800 is not intended to suggest any limitation as to the scope of use or functionality of the invention. Neither should the apparatus 800 be interpreted as having any dependency or requirement relating to any one or combination of components illustrated in the exemplary apparatus 800.

Apparatus 800 may comprise a controller 802, which may be comprised of hardware, software, or a combination of hardware and software. In some embodiments, controller 802 determines the center and width of one or more notches used to isolate ions. For example, controller 802 may perform at least some of the acts described in FIG. 5 and FIG. 6. Apparatus 800 is not limited to a single controller Apparatus 800 may comprise an ion trap 804 and an isolation waveform generator 806. Controller 802 may be coupled to the ion trap 804 and/or isolation waveform generator 806 to allow communication. Any suitable form of coupling may be used. For example, the components may be coupled via a system bus. Alternatively, the components of apparatus 800 may be coupled via a communications network, such as an Ethernet network. Embodiments of the invention are not limited to any specific type of coupling.

Ion trap 804 may be any ion trap suitable for use in mass spectrometry. For example, ion trap 804 may be a quadrapole ion trap, a Fourier transform ion cyclotron resonance (FTICR) MS, or an orbitrap MS.

Isolation waveform generator 806 may be any suitable device for generating the isolation waveforms used to isolate ions in the ion trap 804. For example, isolation waveform generator 806 may be a radio frequency (RF) signal generator.

The inventors have recognized and appreciated that for multiplexed quantitation, using multiple frequency "notches" improves $MS^3$ based isobaric quantitation sensitivity by co-isolating multiple $MS^2$ fragment ions.

Accordingly, aspects of the invention may be embodied as a method for co-isolating a plurality of $MS^2$ product ions labeled with one or more chemical tags using a plurality of m/z ranges, wherein the $MS^2$ product ions are used as $MS^3$ precursor ions. Some aspects may be embodied as an MS apparatus capable of selecting multiple m/z ranges to co-isolate a plurality of $MS^2$ product ions for use as $MS^3$ precursor ions. Some embodiments may be implemented as at least one computer readable medium encoded with instructions that, when executed, perform a method for controlling an MS to co-isolate a plurality of $MS^2$ product ions labeled with one or more chemical tags using a plurality of m/z ranges, wherein the $MS^2$ product ions are used as $MS^3$ precursor ions. The method may be, but is not limited to, the methods described in FIG. 5 and FIG. 6.

Alternatively or additionally, aspects may be embodied as at least one computer readable medium encoded with instructions that, when executed, perform a method for computing notches to use in a multiplexed quantitation and/or to control an MS apparatus to operate with multiple notches.

Though, the invention is not limited to the specific number of stages in an analysis process used to form reporter ions. Further, it should be appreciated that the invention is not limited by the techniques used to break up ions in moving from one stage to the next in the analysis process. Moreover, it should be appreciated that the invention is not limited by the techniques used to isolate ions for further processing.

Accordingly, in other aspects, the invention may be embodied as a method of performing a mass spectrometry analysis.

What is claimed is:

1. A method of performing a mass spectrometry analysis, the method comprising:
    labeling each of a plurality of samples with a corresponding chemical tag selected from a plurality of chemical tags;
    forming a first plurality of ions from molecules in the samples;
    selecting a subset of the first plurality of ions;
    forming a second plurality of ions by fragmenting ions in the subset, the second plurality of ions including a plurality of reporter ions indicative of a relative quantity of each of the plurality of chemical tags present in each of the plurality of samples; and
    measuring the plurality of reporter ions,
    wherein selecting the subset is based, at least in part, on an estimated probability that the subset will generate the plurality of reporter ions.

2. The method of claim 1, wherein selecting the subset is further based on a property of at least a portion of the first plurality of ions selected from the group consisting of an intensity, a mass, a charge, a signal-to-noise ratio, a massto-charge ratio, and a difference in mass-to charge-ratio between at least two of the first plurality of ions.

3. The method of claim 1, wherein selecting the subset of the first plurality of ions comprises ranking at least a portion of the first plurality of ions.

4. At least one non-transitory computer readable medium encoded with instructions that, when executed, perform a method, the method comprising:
   determining the mass-to-charge ratio of a first plurality of ions, wherein each of the plurality of ions is labeled with a chemical tag that produces reporter ions when fragmented;
   determining a conversion efficiency for each of the first plurality of ions, wherein the conversion efficiency represents the probability that an associated ion will produce a reporter ion when fragmented; and
   generating information to control a mass spectrometer to select a subset of the first plurality of ions based on at least one selection criterion, wherein the at least one selection criterion is based at least on the conversion efficiency for each of the first plurality of ions.

5. The at least one non-transitory computer readable medium of claim 4, wherein the at least one selection criterion is further based on a property of at least a portion of the first plurality of ions selected from the group consisting of an intensity, a mass, a charge, a signal-to-noise ratio, a mass-to-charge ratio, and a difference in mass-to charge-ratio between at least two of the first plurality of ions.

6. The at least one non-transitory computer readable medium of claim 4, wherein applying the at least one selection criterion comprises ranking at least a portion of the first plurality of ions based on the at least one selection criterion.

* * * * *